United States Patent [19]

Jackson

[11] Patent Number: 4,829,998

[45] Date of Patent: May 16, 1989

[54] DELIVERING BREATHABLE GAS

[76] Inventor: Richard R. Jackson, One Atlantic Ave., Swampscott, Mass. 01907

[21] Appl. No.: 160,329

[22] Filed: Feb. 25, 1988

[51] Int. Cl.[4] .......................................... A61M 15/00
[52] U.S. Cl. .......................... 128/203.12; 128/203.17; 128/204.18
[58] Field of Search ...................... 128/203.12, 203.17, 128/203.26, 203.27, 203.22, 201.27, 201.13, 200.14, 911, 204.17, 204.18

[56] References Cited

U.S. PATENT DOCUMENTS

| | | | |
|---|---|---|---|
| 369,849 | 9/1887 | Werner et al. | 128/203.22 |
| 1,740,083 | 12/1929 | Galvin | 128/203.26 |
| 3,871,373 | 3/1975 | Jackson | 128/193 |
| 3,968,795 | 7/1976 | O'Neill et al. | 128/201.27 |
| 3,968,812 | 7/1976 | Eross | 137/188 |
| 3,990,442 | 11/1976 | Patneau | 128/194 |
| 4,010,748 | 3/1977 | Dobritz | 128/192 |
| 4,048,993 | 9/1977 | Dobritz | 128/201.13 |
| 4,319,566 | 3/1982 | Hayward et al. | 128/203.12 |
| 4,333,451 | 6/1982 | Paluch | 128/205 |
| 4,391,271 | 7/1983 | Blanco | 128/203.12 |
| 4,396,015 | 8/1983 | Johnson | 128/200.14 |
| 4,417,574 | 11/1983 | Talonn et al. | 128/205.12 |
| 4,456,008 | 6/1984 | Clawson et al. | 128/205.19 |
| 4,459,982 | 7/1984 | Fry | 128/205.14 |
| 4,558,696 | 12/1985 | Eiserman et al. | 128/205.12 |
| 4,621,632 | 11/1986 | Bartels et al. | 128/203.27 |

OTHER PUBLICATIONS

D. G. Revell, 1959, "a Circulation to Eliminate Mechanical Dead Space in Circle Absorption Systems", Can. Anaes. Soc. J., vol. 6, No. 2, pp. 98-103.

*Primary Examiner*—David A. Wiecking
*Assistant Examiner*—Aaron J. Lewis

[57] ABSTRACT

Apparatus for delivering conditioned gas to be breathed by a living being includes a humidifier for conditioning gas provided from a source, inhalation conduit means for conducting an inhalant flow of conditioned gas from the humidifier to the living being, and exhalation conduit means for conducting away gas exhaled by the living being, the inhalation conduit means having a first and a second conduit each extending between and communicating with the humidifier and a delivery point near the living being, gas propulsion apparatus for propelling a carrier flow of gas within the first conduit from the conditioner to the delivery point and within the second conduit from the delivery point to the humidifier, the first and second conduits and the gas propulsion apparatus being adapted to maintain a circulating flow of conditioned gas that includes the inhalant flow and the carrier flow through a loop defined by the first and second conduits, the delivery point, and the humidifier, the demand of the patient being taken from the circulating flow at the delivery point, whereby the gas is conditioned to substantially the same extent at the delivery point as at the humidifier.

15 Claims, 9 Drawing Sheets

DELIVERING BREATHABLE GAS

BACKGROUND OF THE INVENTION

This invention relates to delivering humidified gas mixtures to be breathed by a patient.

In conventional respirator systems a ventilator draws gases from one or more sources and delivers the gas mixture through inhalation and exhalation conduits to and from the patient in cyclic pulses of about 1 liter volume at a rate of about 6-10 pulses per minute. Conventionally the gas is conditioned, by heating or humidifying or by other treatment, before it is delivered to the patient's breathing passages. For example, a nebulizer may be positioned in the inhalation conduit for adding a medication to the gases. Commonly a humidifier, in which the gas mixture is directed over a reservoir of heated water for warming and adding moisture to the gas mixture, is positioned close to the ventilator and remote from the patient in the inhalation conduit. As the gas mixture flows in pulses from the humidifier, its temperature falls so that the temperature of the gas mixture as it leaves the heater is substantially higher than at the point of delivery to the patient. The extent of such a temperature drop varies according to, for example, the length of the hose carrying the gas to the patient, ambient temperatures, and air movement over the hoses.

Humidifiers in common use typically heat the water over which the air being humidified passes, to about 130°-160° F., and systems using such humidifiers commonly require costly and complex apparatus for feedback control to avoid exposing the patient to gases in excess of body temperature. Maintaining the temperature of the gas at the point of delivery to the patient within a range of safety and comfort requires monitoring, e.g., by placing electronic sensors near the patient, and controlling the humidifier thermostatically.

As the temperature of the gas mixture falls, moisture "rains out" of the gas mixture, condensing on the walls of the conduits. Complete obstruction of the inhalant conduit by condensate can result in drowning the patient. Condensate accumulation is generally greater in the expiratory conduit. A collection device is conventionally provided at a low point in the conduit to drain away and trap accumulating condensate.

SUMMARY OF THE INVENTION

In general, in one aspect, the invention features apparatus for delivering conditioned gas to be breathed by a living being that includes a humidifier for conditioning gas available from a source, inhalation conduit means for conducting conditioned gas from the humidifier to the living being, and exhalation conduit means for conducting away gas expired by the living being, in which the inhalation conduit means includes a first and a second conduit each extending between and communicating with the humidifier and a delivery point near the living being, gas propulsion apparatus for propelling a flow of gas within the first conduit from the humidifier to the delivery point and within the second conduit from the delivery point to the humidifier, the first and second conduits and the gas propulsion apparatus being adapted to maintain a circulating flow of conditioned gas that includes the inhalant flow and the carrier flow through a loop defined by the first and second conduits, the delivery point, and the humidifier, the demand of the patient being taken from the circulating flow at the delivery point, whereby the gas is conditioned to substantially the same extent at the delivery point as at the humidifier.

In preferred embodiments the gas propulsion apparatus includes a pump for propelling the carrier flow between and within the first and second conduits (or, less preferably, a first pump for propelling the carrier flow within the first conduit and a second pump for propelling the carrier flow within the second conduit); the pump is driven by an electric motor; the pump and the motor are magnetically linked; the carrier flow is propelled at equal volumetric flow rates (preferably in the range 150-200 liters per minute) within said first and said second conduits; the humidifier is adapted to warm, or, preferably, both to warm the gas (preferably to a temperature within the range between about 20° C. and 45° C.) and to humidify the gas (preferably to saturation); the temperature of the gas is within a range of safety for the patient and the humidity of the gas is within a range of safety for the patient (preferably at saturation) at the delivery point.

In another aspect the invention features a method for delivering conditioned gas to be breathed by a living being, the method including providing a source of gas, conditioning the gas, propelling a flow of the conditioned gas at a rate in excess of the average volumetric flow rate of the inhalant flow cycle of the living being toward and away from a delivery point near the living being, whereby said inhalant flow cycle is taken from said flow.

The improved respiratory apparatus of the invention propels a rapid, high volume carrier flow of gas in a loop from the humidifier, situated some distance from the patient, through a first conduit to the delivery point near the patient and then back again through a second conduit to the humidifier. The inhalation pulse generated by the ventilator passes through the same conduits. As a result of the rapid flow of conditioned gas through the inhalation conduits, the temperature of the gas drops only insubstantially in the inhalant portion of the circuitry, and the gas inhaled by the patient at the delivery point has substantially the same temperature as the gas leaving the conditioner.

As a result, the gas need not at any point in the system be heated to a temperature substantially higher than needed at the point of delivery, so that there is no possibility of accidentally burning the patient's airway. Moreover, temperature sensors can be placed within or at the humidifier itself, rather than at the delivery point, inasmuch as the temperature of the gas as it leaves the humidifier is approximately at or only slightly above the patient's body temperature.

DESCRIPTION OF THE PREFERRED EMBODIMENTS Drawings

FIG. 8b shows a centrifugal pump as adapted for use in FIG. 8, in a view orthogonal to that in FIG. 8a.

PRIOR ART

Figure 1:
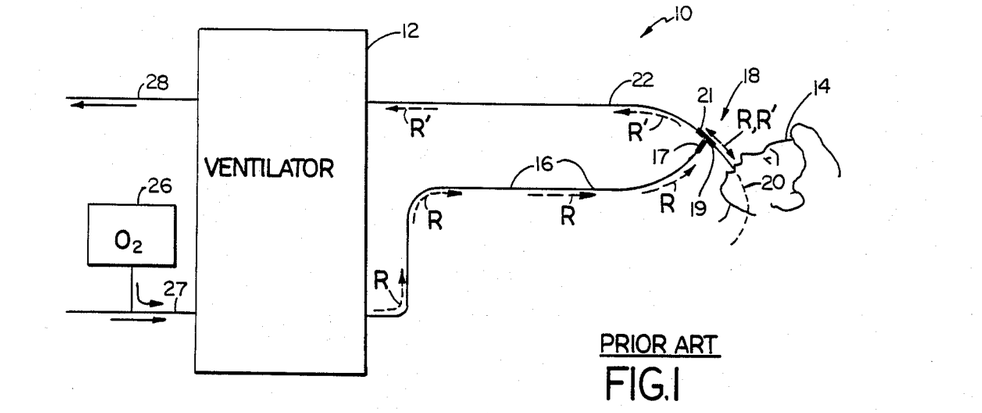
FIGS. 1 and 2 are diagrams of prior art breathing apparatus.

Referring now to FIG. 1, conventional respiratory gas conducting circuitry is shown generally at 10 for conducting respiratory gas between ventilator 12 and patient 14. Gas flows in such circuitry from ventilator 12 through inhalation conduit 16 to stem 17 of a "T" coupling indicated generally at 18. First T arm 19 of T coupling 18 conducts gas to and from oropharyngeal airway 20 implaced in the mouth and throat of patient 14. Second T arm 21 of T coupling 18 conducts gas to exhalation conduit 22, through which gas flows to ventilator 12.

T coupling 18 is provided with valve means (shown in FIGS. 5c and 5d) which have the effect of allowing gas to flow into (but not out of) T coupling 18 via stem 17; thus an inhalant pulse of gas, indicated generally by broken arrows R, leaving ventilator 12 is directed through stem 17 and first T arm 19 into the patient's breathing passages, while an exhalant pulse, indicated generally by broken arrows R', is directed from the patient's breathing passages through T arms 19 and 21 and exhalant conduit 22 to ventilator 12.

Ventilator 12 takes in atmospheric air, shown in FIG. 1 as supplemented by oxygen from source 26, via conduit 27 and exhausts to the atmosphere via conduit 28 gases exhaled by the patient.

Figure 2:
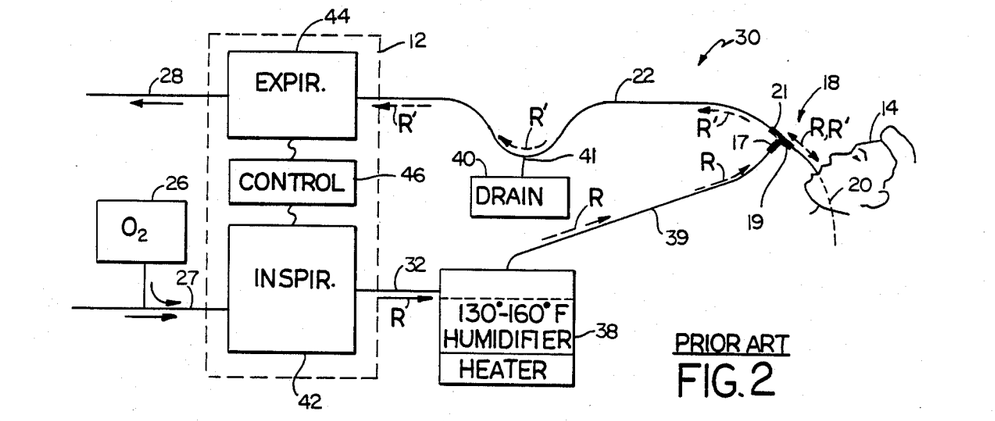

Referring to FIG. 2, alternative conventional respiratory gas conducting circuitry is shown generally at 30. Here gas flows from ventilator 12 through inhalation conduit 32 to humidifier 38. A heater in humidifier 38 heats water to a temperature of 130°–160° F., and this heated water evaporates into the gas flowing over the water, humidifying the gas to a relative humidity about 100% and heating it to a temperature substantially higher than required by the patient. The humidified gas then passes from humidifier 38 through conduit 39 to stem 17 of T coupling 18, described generally above with reference to FIG. 1. First T arm 19 of T coupling 18 conducts gas to and from oropharyngeal airway 20 implaced in the mouth and throat of patient 14. The temperature of the gas has by this point fallen to about the temperature required by the patient, i.e., about 37° C., causing some moisture in the inhalant flow to condense on the luminal walls of conduit 39. Second T arm 21 of T coupling 18 conducts gas to exhalation conduit 22, through which gas flows to ventilator 12.

As gas expired by patient 14 passes through conduit 22 its temperature falls still further, and moisture in the exhalant flow condenses on the luminal walls of conduit 22. Condensate from the exhalant flow flows along the luminal walls of conduit 22 toward low point 41 in conduit 22, and drain 40 is positioned at low point 41 for collecting this condensed moisture.

As shown in FIG. 2, ventilator 12 conventionally includes apparatus 42 for generating the inspiratory (inhalant) flow and apparatus 44 for generating the expiratory (exhalant) flow, and control means 46 for regulating the respiratory pattern.

The respiratory flow through such conventional systems is represented generally by broken arrows, e.g., arrows R (inhalant), R' (exhalant) in FIGS. 1 and 2. The volumetric rate of the respiratory flow (liters per second) fluctuates cyclically according to the breathing rhythm (pattern of ventillation) of the patient. The pattern of ventilation (cycling frequency and amplitude, inhalant and exhalant flow rates, and peak inhalant pressures) can be regulated, as is well-known in the respirator art, by the ventilator alone (particularly for apneic patients), or by the patient's efforts, or by some combination of the ventilator and the patient's efforts.

THE INVENTION

Figure 3:
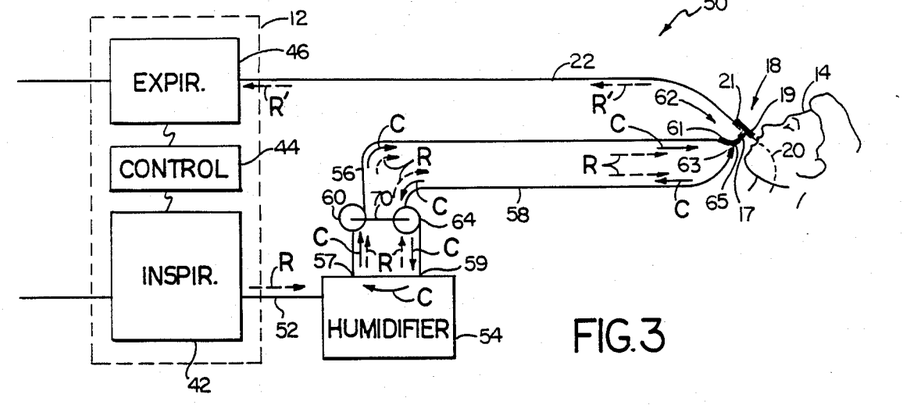
FIG. 3 is a diagram of a breathing apparatus of the invention.

Referring now to FIG. 3, respiratory gas conducting circuitry is shown generally at 50 for conducting respiratory gas between ventilator 12 and patient 14. Inhalation pulses of gas are supplied by ventilator 12 through conduit 52 into humidifier 54, and from humidifier 54 through inhalation conduit means to T coupler 18 near the patient. The inhalation conduit means include first and second conduits 56, 58, a "Y"-coupler shown generally at 62, and centrifugal gas pumps 60, 64. Gas is propelled by pump 60 from humidifier 54 through first conduit 56 to first Y arm 61 of Y coupler 62, and gas is propelled by high-volume pump 64 from second Y arm 63 of Y coupler 62 through second conduit 58. Third Y arm 65 of Y coupler 62 is connected to stem 17 of a T coupler shown generally at 18, which directs gas to and from patient 14 as described generally above with reference to FIGS. 1 and 2. Third Y arm 65 of Y coupler 62 is at the "point of delivery" of the conditioned gas, as that term is used herein.

Pumps 60, 64 are adapted so that they apply equal propulsive strength. As a result when no gas flows from ventilator 12, as, for example during a pause between an exhalant and an inhalant pulse, the net volumetric flow (liters per minute) away from humidifier 54 in conduit 56 equals the net volumetric flow toward humidifier 54 in conduit 58, and there is no flow at the point of delivery to the patient, that is, in third Y arm 65 of Y coupler 62. Pumps 60, 64 provide substantially no resistance to flow in either direction, so that whether or not pumps 60, 64 are operating, any inhalant flow of gas (typically a cyclic pulse, indicated generally by broken arrows R) supplied from ventilator 12 flows substantially without resistance through conduits 56, 58 to Y coupler 62, and from third Y arm 65 of Y coupler 62 to T coupler 18, and through T coupler 18 to patient 14. As a result, the inhalation cycle of the respiratory pattern produced from the ventilator is replicated at the point of delivery.

Pumps 60, 64 can be driven by motors, such as electric motors, separately; to match the propulsive outputs of pumps 60, 64, their respective drivers must be matched. More preferably, pumps 60, 64 are driven in tandem by a single motor, for example by providing pumps 60, 64 with common rotational shaft 70, so that they are assured of having equal velocities.

Pumps 60, 64 are preferably blowers of a centrifugal type, driven by an electric motor. Most preferably the motor is of the brushless explosion-proof high-speed DC type; such motors are quiet and operate well in conditions of high humidity. The motor can be mechanically coupled to each blower, or it can be magnetically coupled to each blower as is well-known in the art of fluid propulsion generally. Mechanically-coupled blowers are commercially available from, for example, Fasco Industries, Inc., St. Louis, MO. Magnetic couplings are known for example in the art of hydraulic pumps, are are commercially available from, for example, Little Giant Pump Co., Oklahoma City, OK.

The relatively rapid, high-volume flow from humidifier 54 through the inhalation conduit means and back to humidifier 54 acts as a "carrier flow", indicated generally by arrows C, as it has the effect of bringing the conditioned gas rapidly to T coupler 18 at a point of delivery near the patient, and at the same time bringing to T coupler 18 at the point of delivery the cyclic pulses of flow produced from ventilator 12.

The carrier flow is preferably at a rate greater than the maximum instantaneous volumetric flow rate of the patient's inhalant flow cycle. Ordinarily the frequency of a patient's ventilation cycle is about 10 cycles per minute or fewer, and the maximum flow to the patient in each cycle is about 10 liters per minute. Most preferably, where the inhalation conduits are standard respiratory hose about 4 or 5 feet long between humidifier and delivery point, the carrier flow rate is in the range 150-200 liters per minute at an occluded pressure approximately 10-15 cm $H_2O$ or less. At such flow rates through such hoses, gas heated to, for example, between 37° C. and 40° C. by the humidifier remains, when it reaches the patient, well within a range of safety and comfort for the patient whose body temperature is normal. That is, the gas will have cooled, if at all, to no lower than 2° below the patient's body temperature of about 37° C. (i.e., to no lower than about 35° C.) by the time it reaches the delivery point. Greater carrier flow rates and pressures can be used, but in case of failure of a connection in the conduit conducting the carrier flow from third Y arms 65 of Y coupler 62 to humidifier 54, the patient can be exposed to the carrier pressure, and high pressures can be dangerous to the patient's airway. A pressure of 10 cm $H_2O$ can be sustained by a patient for long periods without harm.

Humidifier 54 is preferably of a type that can warm the gas to a temperature approximately equal to or slightly greater than the body temperature of the patient, i.e., about 37° C.-40° C., as it humidifies the gas to near saturation, i.e., to a relative humidity of approximately 100%. Preferably the humidifier is additionally capable of warming the gas to temperatures within the broader range 20° C.-45° C., as it humidifies the gas to near saturation, for use in particular patient treatment circumstances in which respiratory gases above or below normal body temperature are required. Most preferably the humidifier is of the type disclosed in my U.S. Pat. No. 3,871,373, in which water vapor passes from a water chamber through a water-vapor permeable wall into a gas conduit for delivery to the patient. Humidifiers of this type can provide air having the appropriate temperature and humidity without raising the temperature of either the water or the gas to substantially higher temperatures.

Figure 4:
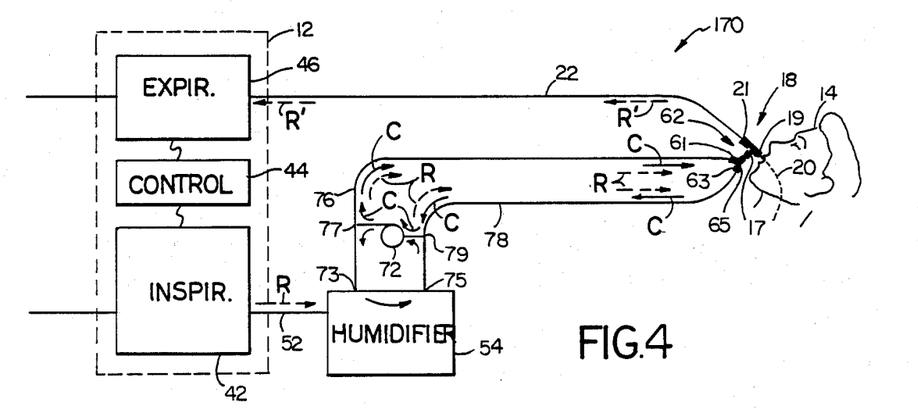
FIG. 4 is a diagram of an alternative breathing apparatus of the invention.

Referring now to FIG. 4, alternative respiratory gas conducting circuitry is shown generally at 170 for conducting respiratory gas between ventilator 12 and patient 14. As in the circuitry shown in FIG. 3, inhalation pulses of gas are supplied by ventilator 12 through conduit 52 into humidifier 54, and from humidifier 54 through inhalation conduit means to T coupler 18 near the patient. In the circuitry shown in FIG. 4 the inhalation conduit means include Y coupler 62, as in FIG. 3, and first and second conduits 76, 78, but in the circuitry of FIG. 4 gas is propelled by single pump 72, which draws gas from conduit 78 at pump connector 79, and sends gas to conduit 76 at pump connector 77, establishing a carrier flow, indicated generally by arrows C, in the portion of the circuit including pump 72, connectors 77, 79, conduits 76, 78, and Y coupler 62; and also a flow in the portion of the circuit including pump 72, connectors 77, 79, and humidifier 54, as is described in more detail below with reference to FIG. 7. The carrier flow is humidified as these two flows intermix within the common portions of connectors 77, 79, and pump 72.

Figure 5:
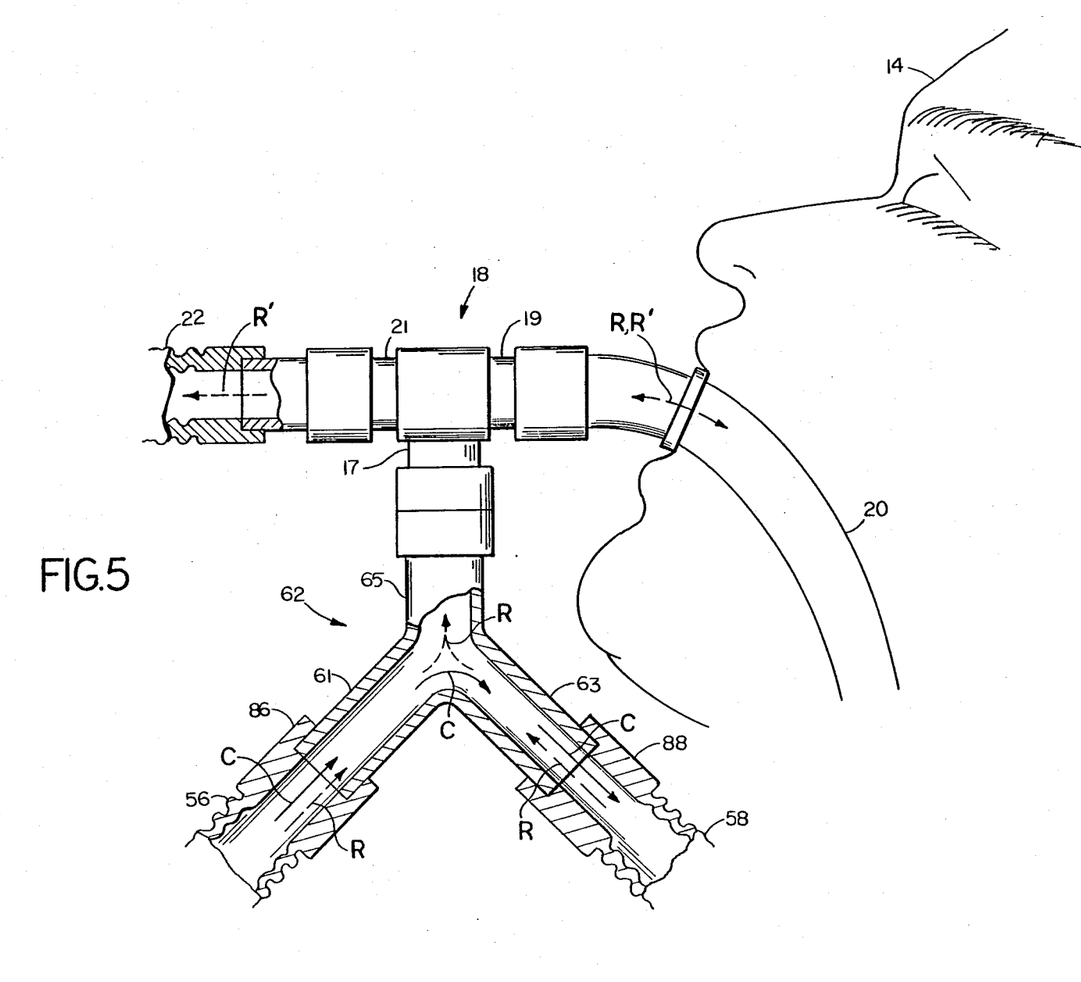
FIG. 5 shows, partly in section, connections with a T coupling near a patient of the inhalant circuit diagrammed in FIGS. 3, 4 or 5.

Referring now to FIG. 5, there are shown in more detail connections of the inhalation conduit means, the Y coupler, and the T coupler near the patient. At the preferred flow rates through such conduits, gas heated to between 37° C. and 40° C. by the humidifier has cooled, if at all, to no lower than 2° C. below the patient's body temperature by the time it reaches the delivery point. Conduits 56, 58 are of standard flexible respirator hose, each having an inside diameter of ⅞ inch (22 mm) and a length of about between 4 and 5 feet. End 86 of first conduit 56 of the inhalation conduit means is connected to second Y arm 61 of Y coupler 62 and end 88 of second conduit 58 of the inhalation conduit means is connected to second Y arm 63 of Y coupler 62. Third Y arm 65 of Y coupler 62 is connected to stem 17 of T coupler 18, which is turn is connected through first T arm 19 to oropharyngeal airway 20 and through second T arm 21 to exhalant conduit 22.

The carrier flow propelled by pumps 60, 64 (not shown in FIG. 5), indicated generally by arrows C, passes through first conduit 56 and first Y arm 61 into Y coupler 62, and then through second Y arm 63 and out of Y coupler 62 through second conduit 58. Because the propelling strengths of pumps 60, 64 are equal, and the carrier flow into Y coupler 62 thus equals the carrier flow out of Y coupler 62, the carrier flow does not itself produce any net flow within third Y arm 65.

A respiratory flow pulse generated by ventilator 12 passes into humidifier 54 and then into the inhalant circuit as described above, and passes into Y coupler 62, as indicated generally by broken arrows R in FIG. 5. The pulse passes into third arm 65 of Y coupler 62, and from there into stem 17 of T coupler 18. The pulse passes to and from the patient's breathing passages as described generally above with reference to FIG. 1. It will be appreciated that, when the carrier flow C is at a flow rate greater than the flow rate of flow R in conduit 58, the net flow in conduit 58 is in the direction of arrows C, that is, away from patient 14.

Figure 5A:
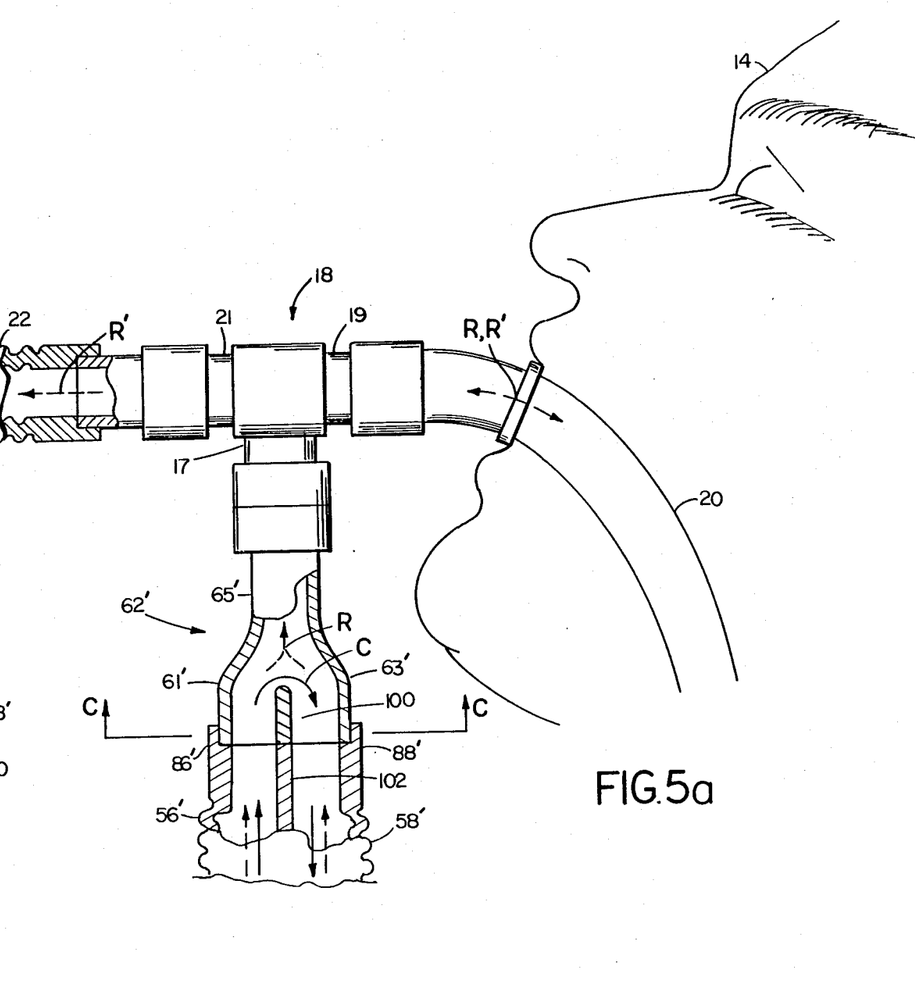
FIG. 5a shows, partly in section, alternative connections with a T coupling near a patient.
Figure 5B:
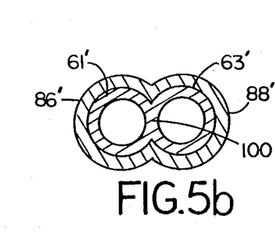
FIG. 5b is a section thru FIG. 5a at C—C.

A more preferred Y coupler is shown generally at 62' in FIGS. 5a and 5b. In this more preferred embodiment, first Y arm 61' and second Y arm 63' are parallel and they have common wall 100, rather than diverging as shown for first and second arms 61, 63 in FIG. 5; and end portions 86', 88' of first and second conduits 56', 58' of the inhalation conduit means are united to have common wall 102. Coupler 62' is connected to conduits 56', 58' by inserting coupler 62' into end portions 86', 88' until common wall 100 of coupler 62' abuts common wall 102 of end portions 86', 88', and a portion of Y arms 61', 63' is slidably engaged within the ends of conduit end portions 86', 88'. Such a configuration provides an added safety feature, as it makes impossible a connection of only one of the two inhalation conduits, requiring instead that whenever one of end portions 86', 88' is operatively connected to Y coupler 62', so also must the other end portion be connected.

Figure 5C:
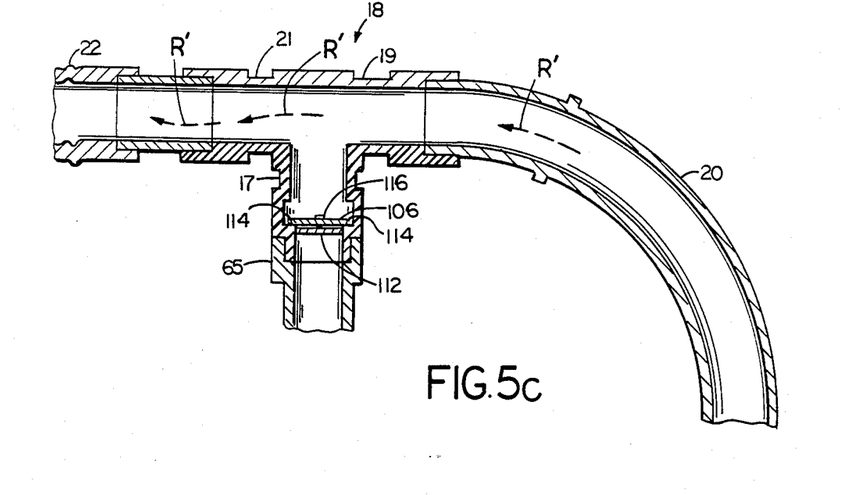
FIG. 5c and 5d show, in section, the operation of a directional control valve in a T coupling.
Figure 5D:
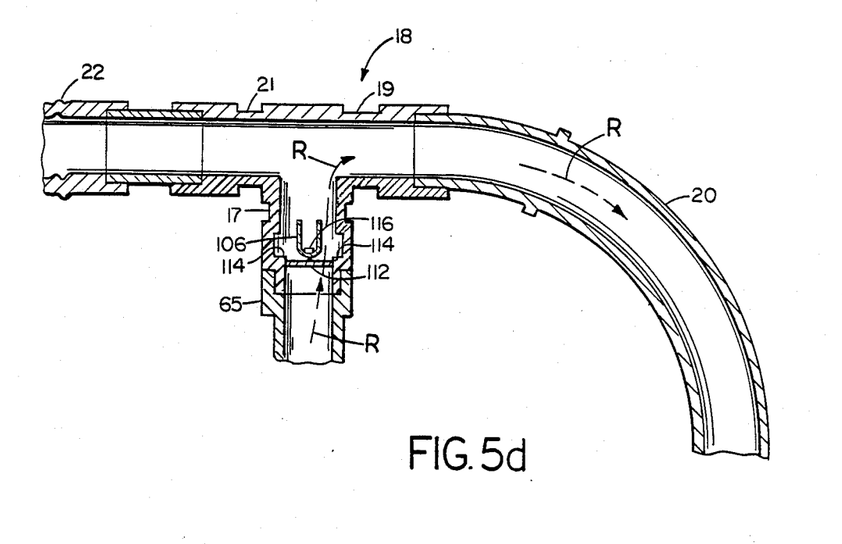

Referring now to FIGS. 5c and 5d, there is shown flap valve 106 in stem 17 of T connector 18, for controlling the direction of gases passing to and from the patient as described generally above with reference to FIG. 1. Flap valve 106 is a disc, preferably constructed of a flexible lightweight material having a good elastic memory, such as, e.g., silicone rubber. The lumen of stem 17 is provided with annular seat 114 upon which the margin of valve 106 rests when valve 106 is pressed flat away from the intersection of T arms 19, 21, and stem 17, substantially preventing movement of gases from T coupler 18 into third Y arm 65. Valve 106 is flexibly connected, in well-known a manner, by pin 116 to crosspiece 112, which traverses the lumen of stem 17. As shown in FIG. 5d, an inhalant stream R from the respirator (not shown), opens valve 106 by flexing it away from seat 114 and away from the wall of stem 17, as it flows past crosspiece 112 and valve 106, from third Y arm 65, and passes on via oropharynegal airway 20 to the patient (not shown). As shown in FIG. 5c, an exhalant stream R' from the patient (not shown), passing via oropharyngeal airway 20 into T coupler 18, closes flap valve 106 by pressing its margin against seat 114, as it flows from T coupler 18 into exhalant conduit 22.

Figure 6:
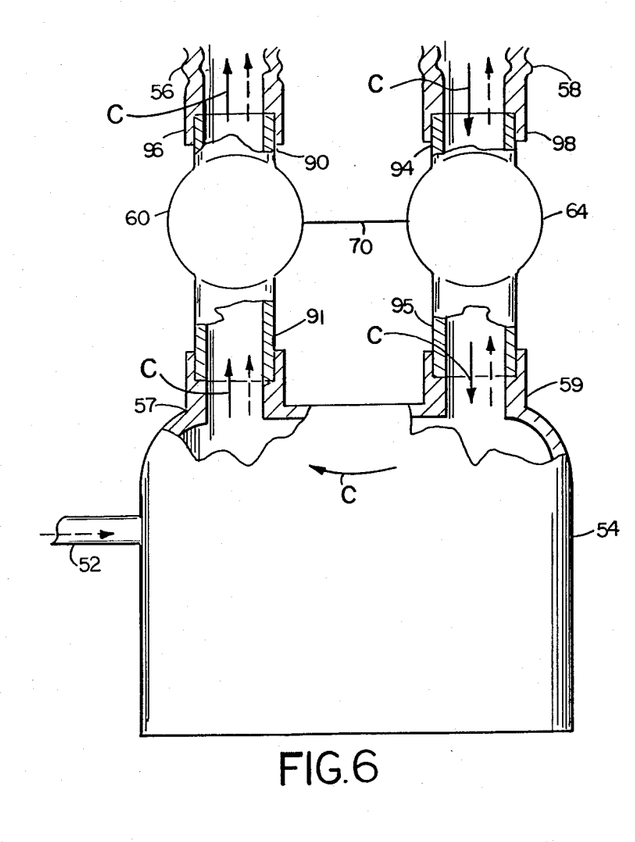
FIG. 6 shows, partly in section, connections with a humidifier of the inhalant circuit diagrammed in FIG. 3.

Referring now to FIG. 6, there are shown in more detail connections to humidifier 54 of the inhalation conduit means diagrammed in FIG. 3. End 96 of first conduit 56 of the inhalation conduit means is connected to output port 90 of centrifugal gas pump 60, and input port 91 of pump 60 is connected to first port 57 on humidifier 54; end 98 of second conduit 58 of the inhalation conduit means is connected to input port 94 of centrifugal gas pump 64, and output port 95 of pump 64 is connected to second port 59 on humidifier 54. Pump 60 thus propels gas away from humidifier 54 through first conduit 56 to Y coupler 62 (not shown in FIG. 6), and pump 64 propels gas from Y coupler 62 through first conduit 56 toward humidifier 54. Within humidifier 54 the carrier flow (shown generally by arrows C) passes from second port 59 to first port 57. Pumps 60, 64 are preferably driven on common shaft 70, so that they are assured of having equal rotational velocities, as described generally above with reference to FIG. 3.

Figure 7:
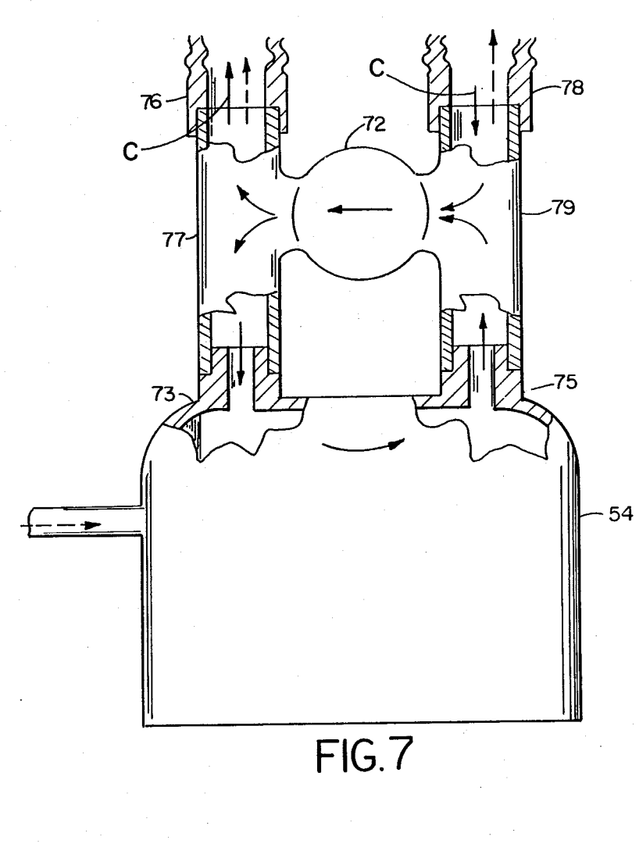
FIG. 7 shows, partly in section, connections with a humidifier of the inhalant circuit diagrammed in FIG. 4.

Referring now to FIG. 7, there are shown in more detail connections to humidifier 54 of the inhalation conduit means diagrammed in FIG. 4. First conduit 76 of the inhalation conduit means is connected via pump connector 77 to first port 73 on humidifier 54, and second conduit 78 of the inhalation conduit means is connected via pump connector 79 to second port 75 on humidifier 54. In this embodiment single centrifugal gas pump 72 is interposed between conduits 76, 78 by connections with pump connectors 77 and 79, respectively. Pump 72 propels gas from second conduit 78 via connector 79 to first conduit 76 via connector 77. A portion of the gas drawn by pump 72 from second conduit 78 arrives at connector 79 from humidifier 54 via port 75, and a portion of the gas propelled by pump 72 into first conduit 76 departs from connector 77 into humidifier 54 via port 73. Within humidifier 54 gas flows generally from port 73 to port 75. Another portion of the gas drawn by pump 72 from second conduit 78 arrives at connector 79 from Y coupler 62 (not shown in FIG. 7), and a portion of the gas propelled by pump 72 into first conduit 76 departs from connector 77 toward Y coupler 62, setting up a carrier flow between pump 72 and Y coupler 62. The cross-sectional area of the lumen of each of ports 73, 75 is reduced in relation to the cross-sectional area of the lumen of each of conduits 76, 78, and this reduction effects a reduced volumetric rate of flow through ports 73, 75 as compared with the flow through conduits 76, 78. In consequence, the volumetric flow rate propelled by pump 72 from second conduit 78 to first conduit 76 is divided into a greater carrier flow rate through conduits 76, 78, pump 72 and the point of delivery and a lesser flow rate through ports 73, 75, pump 72, and humidifier 54. Between connectors 79 and 77 the carrier flow between pump 72 and the point of delivery mixes with the flow passing from connector 77 through port 73, through the interior of humidifier 54, and through port 75 back to connector 79, as the two flows pass through pump 72, and the carrier flow is thereby warmed and humidified. Suitable flow rates are, for example, a greater carrier flow of 65 liters/minute (passing to the delivery point) and a lesser flow of 35 liters/minute (passing through humidifier 54), generated by a pump 72 that provides a combined flow of 100 liters/minute.

Figure 7A:
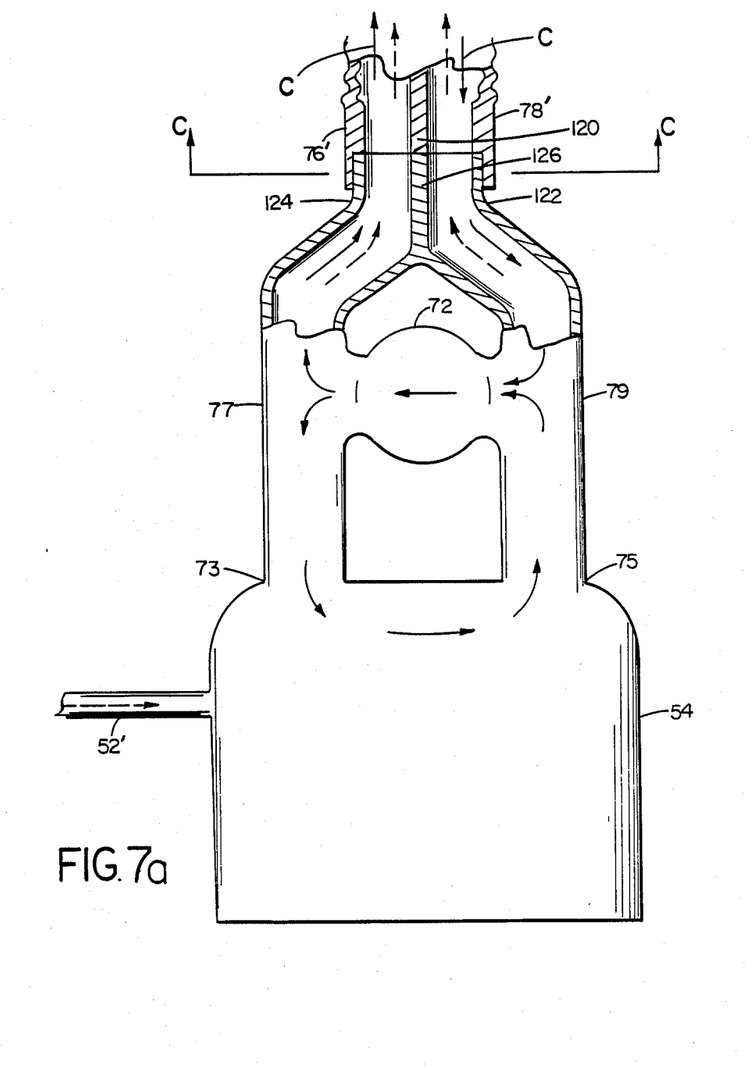
FIG. 7a shows, partly in section, alternative connections with a humidifier of the inhalant circuit diagrammed in FIG. 4.
Figure 7B:
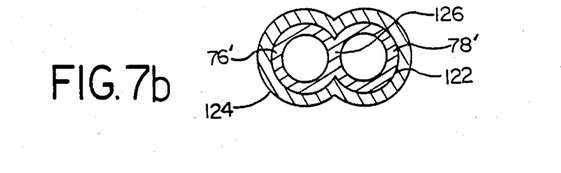
FIG. 7b is a section thru FIG. 7a at C—C.

Referring now to FIG. 7a and 7b, there is shown a more preferred connection of humidifier 54 to the inhalation conduit means diagrammed in FIG. 4. Here ends 76', 78' of the inhalation conduit means share common wall 120, and connectors 122, 124 to pump 72 share common wall 126. Ends 76', 78' of the inhalation conduit means are connected to pump connectors 122, 124, in a fashion analogous to that described above with reference to FIGS. 5a and 5b. This arrangement, together with the more preferred Y coupler described above with reference to FIGS. 5a and 5b, makes it impossible to operate the apparatus with only the first conduit connected to the humidifier, which would create a potential of overpressuring the patient; or with only the second conduit connected to the humidifier, whereby the patient would not be supplied with conditioned gas as desired.

Conduits 56', 58' can be of standard flexible respirator hose, separate over most of their length and modified at their end portions 86', 88', as described above with reference to FIGS. 5a and 5b, and at their opposite ends 76', 78'. More preferably conduits 56', 58' are joined over their entire length, sharing a common wall, and most preferably they are double-extruded tubing; or one of the conduits 56', 58' is enclosed within the other. Such configurations allow heat to pass from the warmer air mass across the common wall to the cooler air mass, further tending to equalize the temperature of the air supply in the carrier loop.

Figure 8:
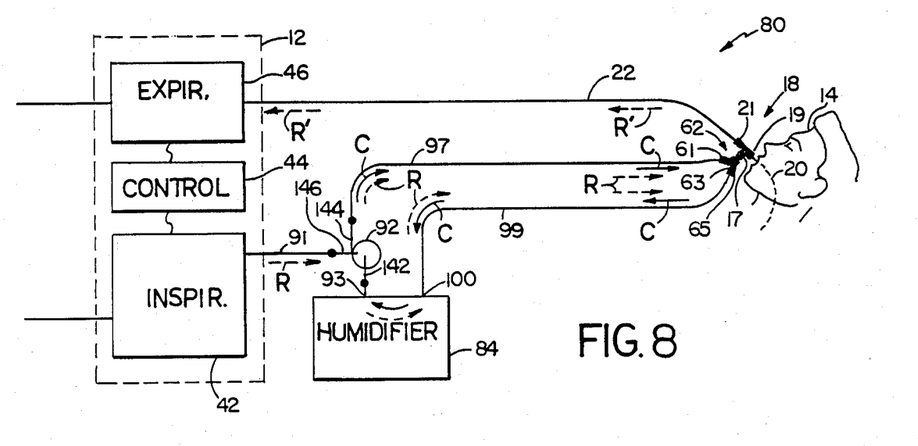
FIG. 8 is a diagram of an alterative breathing apparatus of the invention.

The inhalation pulses of gas from the source can be supplied to a point in the gas conducting circuitry other than at the humidifier. For example, in a preferred embodiment shown diagrammatically in FIG. 8 and semidiagrammatically in FIGS. 8a and 8b, gas supplied by the ventilator is delivered to the inhalation conduit means at a centrifugal pump adapted to propel a carrier flow between the humidifier and the point of delivery. Referring now to FIG. 8, respiratory gas conducting circuitry is shown generally at 80 for conducting respiratory gases between ventilator 12 and patient 14. Centrifugal gas pump 92 draws humidified as from humidifier 84 via humidifier port 93 and propels the gas through first conduit 97 toward the point of delivery at Y coupler 62; as gas is so removed from humidifier 84, it is replaced by gas returning from the point of delivery at Y coupler 62 through second conduit 99 via humidifier port 100 to humidifier 84. Thus when no gas flows from ventilator 12, the net volumetric flow away from humidifier 84 in conduit 97 equals the net volumetric flow toward humidifier 84 in conduit 99, and there is no flow at the point of delivery to the patient, that is, in third Y arm 65 of Y coupler 62. The inhalation cycle of the respiratory pattern is introduced into the carrier flow by conducting the gas supplied by the ventilator through conduit 103 into centrifugal pump 92, as can be understood with reference to FIGS. 8a and 8b.

Figure 8A:
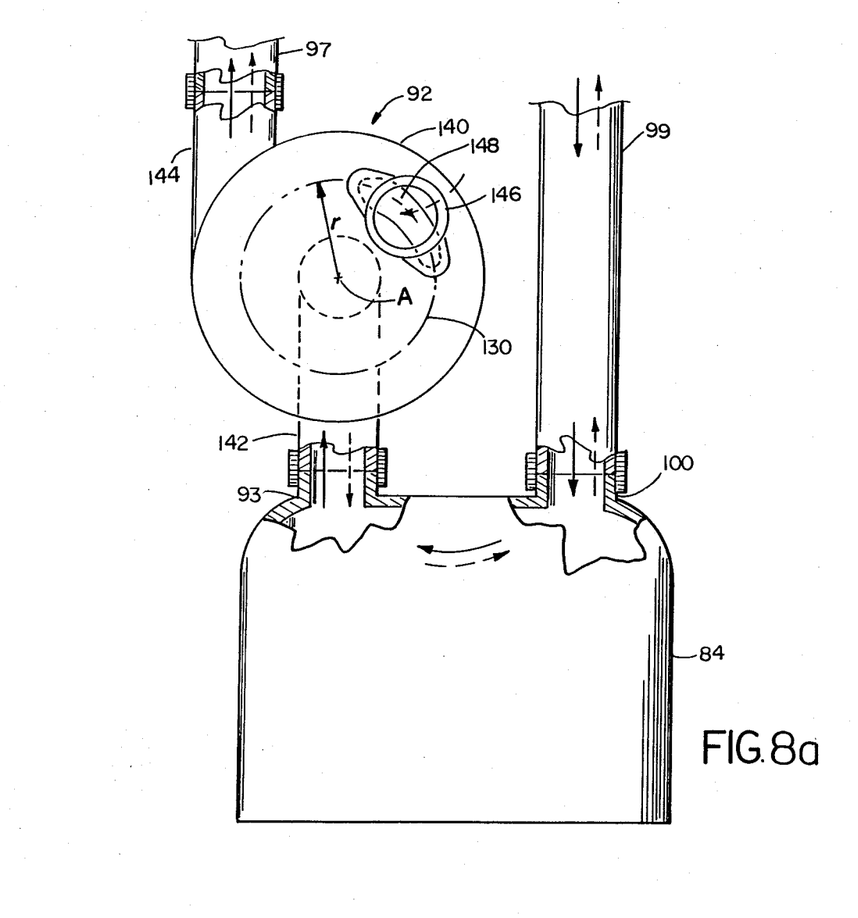
FIG. 8a shows, partly in section, connections with a humidifier of the inhalant circuit diagrammed in FIG. 8.

FIG. 8a shows in more detail connections to humidifier 84 of the inhalation conduit means diagrammed in FIG. 8. A centrifugal pump, shown semidiagrammatically in FIGS. 8a and 8b and indicated generally at 92, includes housing 140 containing a centrifugal fan (not shown), pump intake conduit 142 and pump output conduit 144, as is conventional for centrifugal pumps. The centrifugal fan, driven in conventional fashion by a motor (not shown), rotates upon axis A—A, propelling air by centrifugal action away from rotational axis A—A and toward the circumference of housing 140; as a result air pressure near axis A—A is reduced to below atmosphere and air pressure near the circumference is raised above atmosphere. As is known of centrifugal pumps generally, the pressure within the housing substantially equals atmospheric pressure at points which describe a circle 130, located intermediate axis A—A and the circumference. Circle 130, which describes the locus of points at which the internal pressure equals atmospheric pressure, is at a distance r from axis A—A, which distance is characteristic of the particular pump design, and which can be determined from the specifications for the particular pump, or from well known theoretical considerations, or by trial, without undue experimentation.

Figure 8B:
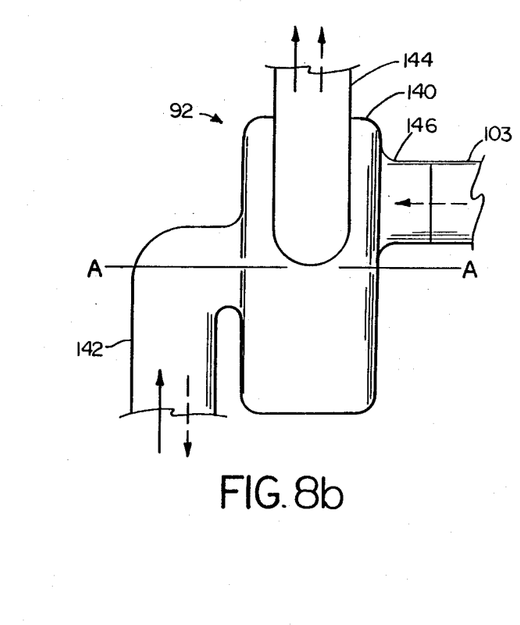

Pump intake conduit 142 communicates with the interior of housing 140 through the housing wall near axis A—A, and output conduit 144 communicates with the interior of housing 140 through the housing wall near the circumference; and when air flow is permitted in pump intake and output conduits 142, 144, a flow of air, indicated in FIGS. 8, 8a, and 8b by arrows C is propelled into pump 92 via pump intake conduit 142 and away from pump 92 via pump output conduit 144. The flow from pump 92 via pump output conduit 144 through conduit 97 to the delivery point at Y coupler 62 and from the delivery point at Y coupler 62 through conduit 99 to humidifier 84 and from humidifier 84 back to pump 92 via pump input conduit 142 describes a carrier flow circuit for this embodiment. The volumetric flow rate of this carrier flow, propelled by pump 92, passing from pump 92 to the delivery point in Y coupler 62 substantially equals the volumetric flow rate of the carrier flow, drawn by pump 92, passing to pump 92 from the delivery point in Y coupler 62 by way of the humidifier. Aperture 148 is provided through the housing wall at about radial distance r from A—A for introduction into the inhalation circuit of inhalant pulses from the ventilator.

Pump 92 is provided with flange 146, situated in operative relation to aperture 148 to provide for connection of centrifugal pump 92 via flange 146 with conduit 103, so as to permit flow of air provided from ventilator 12 through conduit 103, flange 146, and aperture 148 into pump 92. When no gas is delivered by ventilator 12 through conduit 91 into pump 92 via flange 146 and aperture 148, as for example during a pause between an exhalant and an inhalant pulse, there is no net flow of gas to the patient through third Y arm 65 of Y coupler 62. Pump 92 provides substantially no resistance to flow in either direction, so that whether or not pump 92 is operating, any inhalant flow of gas supplied from ventilator 12 flows substantially without resistance through conduits 97, 99 to Y coupler 62, and from third Y arm 65 of Y coupler 62 to T coupler 18, and through T coupler 18 to patient 14, as described generally above with respect to FIGS. 5 and 5—d. When pump 92 is operating the carrier flow has the effect described above of bringing the conditioned gas rapidly to T coupler 18 at a point of delivery near the patient, and at the same time bringing to T coupler 18 at the point of delivery the cyclic pulses of flow produced from ventilator 12.

A conventional centrifugal pump of the kind, for example, described above with reference to FIG. 3 can be adapted for use in the preferred embodiment described with reference to FIGS. 8, 8a, and 8b, by drilling or cutting the housing at the desired location to provide aperture 148, and affixing flange 146 thereto. Or, a housing 140 can be specially fabricated as required.

OTHER EMBODIMENTS

Other embodiments are within the following claims. For example, conduits 56, 58 (or 76, 78 or 97,99) can be joined lengthwise over at least part of their length so that they share a portion of a conduit wall between them; to the extent that the common wall conducts heat from the warmer of the air masses running within the conduits, that portion of the carrier flow returning from the delivery point to the humidifier can be warmed within across the common conduit wall by that portion of the carrier flow that runs from the humidifier to the point of delivery, further reducing the temperature drop in the inhalant conduit means. This effect can be especially pronounced if one conduit of the inhalation conduit means is enclosed over at least a portion of its length by the other.

As will be appreciated by one skilled in the art of supplying gas for breathing, styles of connectors and couplers can used with the invention that differ in particulars from those described and shown in the drawings herein. For example, the "Y" and "T" couplers can be other than Y- and T-shaped; and their coupling functions can be performed by a coupler combining these parts in a single unit.

The air propulsion apparatus can be adapted for intermittent operation by trained personnel at higher carrier flow rates and pressures for flushing through any condensate that may accumulate in the inhalant conduits without interrupting of the patient's breathing cycle. Or, an auxiliary pump, operating at higher flow rates and pressures, can be connected in series fashion for intermittent higher-flow and -pressure operation. Carrier flow rates of about 150–200 liters per minute can be suitable for such flushing. Thus, while such higher carrier flow rates and pressures may pose a potential hazard to the patient in case of interruption of flow in one of the inhalant conduits, they can be used under supervision.

I claim:

1. Apparatus for delivering conditioned gas to be breathed by a living being, comprising a humidifier for conditioning gas provided from a source, inhalation conduit means for conducting an inhalant flow of conditioned gas from said humidifier to said living being, and exhalation conduit means for conducting away gas exhaled by said living being, said inhalation conduit means comprising     a first and a second conduit each extending between and communicating with said humidifier and a delivery point near said living being,     gas propulsion means for propelling a carrier flow of gas within said first conduit from said conditioner to said delivery point and within said second conduit from said delivery point to said humidifier,     means including said first and second conduits and said gas propulsion means for maintaining a circulating flow of conditioned gas comprising said inhalant flow and said carrier flow through a loop defined by said first and second conduits, said delivery point, and said humidifier, the demand of the patient being taken from said circulating flow at said delivery point,     whereby said gas is conditioned to substantially the same extent at said delivery point as at said humidifier.

2. The apparatus of claim 1, wherein said gas propulsion means comprises a pump for propelling said carrier flow between and within said first and said second conduits.

3. The apparatus of claim 1, wherein said gas propulsion means comprises a first pump for propelling said carrier flow within said first conduit and a second pump for propelling said carrier flow within said second conduit.

4. The apparatus of claim 2, wherein said pump is driven by an electric motor.

5. The apparatus of claim 3, wherein each of said first and said second pumps is driven by an electric motor.

6. The apparatus of claim 4, wherein said electric motor is magnetically linked to said pump.

7. The apparatus of claim 1, wherein said gas propulsion means is adapted to generate said carrier flow at equal volumetric flow rates within said first and said second conduits.

8. The apparatus of claim 1, wherein said carrier flow is propelled by said gas propulsion means at a volumetric flow rate in the range 150 - 200 liters per minute.

9. The apparatus of claim 1, wherein said humidifier is adapted to warm said gas.

10. The apparatus of claim 9, wherein said humidifier is adapted to warm said gas to a temperature within the range between about 20° C. and 45° C.

11. The apparatus of claim 1, wherein said humidifier is adapted to humidify said gas.

12. The apparatus of claim 1, wherein said humidifier is adapted to humidify said gas to saturation.

13. The apparatus of claim 1, wherein said condition is the temperature of said gas, and said temperature is within a range of safety for said patient at said delivery point.

14. The apparatus of claim 1, wherein said condition is the relative humidity of said gas, and said relative humidity is within a range of safety for said patient at said delivery point.

15. The apparatus of claim 14, wherein said relative humidity is at saturation at said delivery point.

* * * * *

UNITED STATES PATENT AND TRADEMARK OFFICE
CERTIFICATE OF CORRECTION

PATENT NO. : 4,829,998

DATED : May 16, 1989

INVENTOR(S) : Jackson

It is certified that error appears in the above-identified patent and that said Letters Patent is hereby corrected as shown below:

ON THE TITLE PAGE:
Other Publications: D.G. Revell, first word of title should be --A-- instead of "a".
Col. 2, line 56, "Drawings" should be on a new line.
Col. 3, line 11, "alterative" should be --alternative--.
Col. 5, line 8, "are" should be --and--.
Col. 7, line 24, "oropharynegal" should be --oropharyngeal--.
Col. 8, line 66, "as" should be --gas--.
Col. 10, line 12, "5--d" should be --5a-d--.
Col. 10, line 55, "interrupting" should be --interruption--.

Signed and Sealed this

Sixteenth Day of January, 1990

Attest:

JEFFREY M. SAMUELS

*Attesting Officer*     *Acting Commissioner of Patents and Trademarks*